(12) United States Patent
Georgopoulos et al.

(10) Patent No.: US 10,993,951 B2
(45) Date of Patent: *May 4, 2021

(54) FOSFOMYCIN FORMULATION FOR PARENTERAL ADMINISTRATION

(71) Applicants: Apostolos Georgopoulos, Vienna (AT); Albert Schifer, Vienna (AT); Wolfgang Rous, Vienna (AT)

(72) Inventors: Apostolos Georgopoulos, Vienna (AT); Albert Schifer, Vienna (AT); Wolfgang Rous, Vienna (AT)

( * ) Notice: Subject to any disclaimer, the term of this patent is extended or adjusted under 35 U.S.C. 154(b) by 0 days.

This patent is subject to a terminal disclaimer.

(21) Appl. No.: 16/869,646

(22) Filed: May 8, 2020

(65) Prior Publication Data
US 2020/0261478 A1 Aug. 20, 2020

Related U.S. Application Data

(63) Continuation of application No. 16/082,590, filed as application No. PCT/EP2017/056252 on Mar. 16, 2017, now Pat. No. 10,675,291.

(30) Foreign Application Priority Data

Mar. 16, 2016 (EP) .................... 16160698

(51) Int. Cl.
| | | |
|---|---|---|
| *A61K 31/665* | (2006.01) | |
| *A61K 9/08* | (2006.01) | |
| *A61K 9/00* | (2006.01) | |
| *A61K 47/12* | (2006.01) | |

(52) U.S. Cl.
CPC .......... *A61K 31/665* (2013.01); *A61K 9/0019* (2013.01); *A61K 9/0029* (2013.01); *A61K 9/08* (2013.01); *A61K 47/12* (2013.01)

(58) Field of Classification Search
CPC .................................................. A61K 31/665
See application file for complete search history.

(56) References Cited

U.S. PATENT DOCUMENTS

| 8,980,226 B2 | 3/2015 | Baker et al. | |
|---|---|---|---|
| 10,675,291 B2 * | 6/2020 | Georgopoulos | A61K 9/0019 |
| 2005/0014829 A1 * | 1/2005 | Remenar | C07C 211/42 |
| | | | 514/554 |
| 2015/0057241 A1 | 2/2015 | Montgomery | |
| 2015/0057242 A1 | 2/2015 | Montgomery | |
| 2015/0132382 A1 * | 5/2015 | Dedhiya | A61K 31/665 |
| | | | 424/482 |

FOREIGN PATENT DOCUMENTS

| DE | 202008012514 U1 | 11/2008 |
|---|---|---|
| EA | 021876 B1 | 9/2015 |
| WO | 2004063036 A1 | 7/2004 |
| WO | 2005110022 A2 | 11/2005 |

OTHER PUBLICATIONS

Marschall's CAS: 150:83907, 2009.*
Bundgaard H. et al. "Acid-Catalyzed Hydrolysis of Fosfomycin and Its Implication in Oral Absorption of the Drug" International Journal of Pharmaceutics, 1980 , V.6, pp. 1-9.
Office Action, RU 2018134749/04 dated May 21, 2020.
Gibson, Ronald L et al. "Pathophysiology and Management of Pulmonary Infections in Cystic Fibrosis" Am J Respir Crit Care Med vol. 168. pp. 918-951, 2003.
Lyczak, Jeffrey B. et al., "Lung Infections Associated with Cystic Fibrosis" Clinical Microbiology Reviews, Apr. 2002, p. 194-222.
Quentin, Claudine et al., "Stability of fosfomydn and qidnoloaes in peritoneal dialysis solution" Journal of Antimicrobial Chemotherapy, vol. 25, Issue 5, May 1, 1990, pp. 878-880.
Baile, George R. et al., "Stability of Drug Additives to Peritoneal Dial Ysa Te" Peritoneal Dialysis International, (1995) vol. pp. 328-335.

* cited by examiner

*Primary Examiner* — Rei Tsang Shiao
(74) *Attorney, Agent, or Firm* — Edwin S. Flores; Daniel J. Chalker; Chalker Flores, LLP

(57) ABSTRACT

The field of the present invention is that of fosfomycin formulations for parenteral administration, in particular for intravenous administration. Formulations of the prior art provide fosfomycin as a powder to be diluted directly prior to the administration. The aim of the invention is to provide a fosfomycin formulation for parenteral administration which is easier to produce and administer or which lowers the risk of puncture injuries for healthcare professionals and the health risks for the patients (for example due to contamination or incorrect dosages) by preventing additional processing steps. During the course of the invention, it was surprisingly shown that fosfomycin is much more stable in an aqueous solution than what is commonly assumed. The invention therefore provides a closed container which contains an aqueous solution for parenteral administration, wherein at least one pharmaceutically acceptable salt of fosfomycin, in particular fosfomycin disodium salt, and a pharmaceutically acceptable acid, in particular succinic acid, are dissolved in the solution. Preferred containers are breakable ampoules made of plastic or glass, puncturable vials, infusion bags, or syringes ready for injection.

15 Claims, 2 Drawing Sheets

FOSFOMYCIN FORMULATION FOR PARENTERAL ADMINISTRATION

CROSS-REFERENCE TO RELATED APPLICATIONS

This application is a continuation application of U.S. patent application Ser. No. 16/082,590 filed Sep. 6, 2018, which is a National Stage of International Application No. PCT/EP2017/056252, filed on Mar. 16, 2017 claiming the priority of EP 16160698.3, filed on Mar. 16, 2016, the content of each of which is incorporated by reference herein.

TECHNICAL FIELD OF THE INVENTION

The field of the present invention is that of fosfomycin formulations for parenteral administration, particularly for intravenous administration.

STATEMENT OF FEDERALLY FUNDED RESEARCH

None.

INCORPORATION-BY-REFERENCE OF MATERIALS FILED ON COMPACT DISC

None.

BACKGROUND OF THE INVENTION

The antibiotic fosfomycin is a structurally unique substance within the antibiotics and was originally isolated from *Streptomyces fradiae*. Parenterally, fosfomycin is administered intravenously or intramuscularly, for example, and is commonly used for targeted therapy of infections in particular in the medical critical care, especially if resistance or intolerance can be expected with regard to other antibiotics. Clinical applications for the use of fosfomycin are among others: in the area of the central nervous system, meningitis, meningoencephalitis, cerebral abscess, and subdural emphysema; in surgery, postoperative infections, concomitant infections in tumors and prostatitis; in orthopedics and traumatology, postoperative bone infections (infected osteosynthesis, endoprosthesis), osteomyelitis, purulent arthritis, abscesses, and phlegmons; in the area of the respiratory tract, bronchopneumonia, pulmonary abscess, and sinusitis; and sepsis.

Fosfomycin disodium salt is a common pharmaceutically acceptable salt of fosfomycin. It is a white or almost white, very hygroscopic powder that is highly soluble in water. Fosfomycin which is dissolved in water cannot be administered parenterally due to the high pH value of the solution. In order to achieve a tissue-compatible or vein acceptable pH, succinic acid is therefore added to currently available preparations for parenteral administration.

Currently, succinic acid is added in the form of a powder by sterile mixing it with fosfomycin as a powder. This mixture is filled as a powder into puncturable vials and put on the market in this form. In this form of a dry substance for infusion preparation approved in individual countries of the European Union are for example Fosfomycin Astro (Astro-Pharma GmbH, Vienna, AT), Fosfomycin medicamentum (medicamentum pharma GmbH, Allerheiligen, AT) und Fosfomycin Sandoz® (Sandoz GmbH, Kundl, AT) in Austria, Fosfomycin Infectopharm® (Infectopharm Arzneimittel und Consilium GmbH, Heppenheim, DE) in Germany, and Fomicyt® (Infectopharm Arzneimittel und Consilium GmbH, Heppenheim, DE) in the United Kingdom.

Directly prior to the parenteral administration such dry substances have to be dissolved in a suitable solvent by the medical personnel.

The current procedure causes various problems. The physical sterile mixing of dry substances is very complex as it is necessary, for example, to ensure the uniformity of the mixture, i.e. no demixing or caking of the powder must occur. This requires a complicated technology which is mastered only by a few manufacturers under the required Good Manufacturing Practice (GMP) conditions. This results in ongoing supply shortages in the supply of fosfomycin for parenteral administration. For example, according to an information from the Federal Office for Safety in Health Care, all formulations of fosfomycin approved for parenteral administration have been unavailable in Austria since June 2015 and are expected to remain unavailable until at least March 2016 (status as of February 2016).

In addition, the processing step required by the health care professionals to obtain a solution for infusion poses a health risk for both the personnel and the patient, especially if the susceptibility to human error is increased by a high workload. Firstly, the processing step itself poses an additional risk of puncture wounds to the personnel. Secondly, the risk of a dangerous contamination or wrong dosage to the patient is increased by the additional processing step. And thirdly, when the dry substance contains, as usual, fosfomycin disodium salt (regular doses of about 4 to 8 grams include about 60 to 120 mmol sodium ions), and the dry substance is dissolved, due to an error and contrary to the package information leaflet, in physiological saline and is administered in this way, the patient may suffer a sometimes fatal hypernatremia due to the excess of sodium ions resulting from this.

Some of these problems are also recognized by DE 20 2008 012 514 U1. This document proposes as an approach a packaging unit for providing a parenterally administrable, pharmacologically acceptable pharmaceutical formulation, comprised of the antibiotic fosfomycin and succinic acid or another biocompatible acid, characterized in that the unit consists of one container which is sterile filled with fosfomycin in powder form, and another container which is sterile filled with the acid, dissolved in an pharmacologically acceptable solvent.

SUMMARY OF THE INVENTION

An object of the present invention is hence to provide a fosfomycin formulation for parenteral administration aimed at overcoming the disadvantages of the prior art such as, inter alia, delivery bottlenecks due to elaborate manufacturing and hazardous further processing steps just prior to administration, which, for example, are still needed in the approach of DE 20 2008 012 514 U1. This means, it is an object of the present invention to provide a fosfomycin formulation für parenteral administration which is easier to produce and to administer.

Surprisingly, it was demonstrated in the course of the present invention that fosfomycin is much more stable in an aqueous solution than was commonly assumed. In the course of the present invention, the stability of fosfomycin in an aqueous solution in the presence of an acid was tested at different temperatures and time periods. Even after repeated autoclaving at 125° C. and months of storage fosfomycin was effective against the tested bacteria such as *Staphylococcus* and *Escherichia* (see example 2 and FIGS. 1A-1D).

Therefore, the present invention provides a closed container which contains an aqueous solution for parenteral administration, wherein a pharmaceutically acceptable salt of fosfomycin and a pharmaceutically acceptable acid are dissolved in said solution. In the solution, further active ingredients and/or excipients may be included. It is convenient if the container is hermetic (or "hermetically sealed"), which, in other words, means that no gas exchange between the solution and the environment of the container is possible.

To reach to the present invention, the inventors had to overcome a deeply rooted prejudice in the prior art:

All fosfomycin formulations for parenteral administration of the prior art have in common their creators' assumption that fosfomycin is too unstable in solution and must thus be used as a powder in the formulation and must be dissolved just prior to administration. This prejudice is so deeply rooted in the prior art that, for example, the dry powder mixing of fosfomycin and succinic acid under GMP conditions is performed under enormous effort, and that supply constraints, as set forth above, are accepted.

Thus, the Public Assessment Report (PL 15011/0014 of 1 Sep. 2014) of Medicines & Healthcare Products Regulatory Agency (MHRA) recommends for Fomicyt® to only use freshly prepared solution. The chemical stability of the ready-to-use, sterile-prepared solution is indicated to be 12 hours at 2-8° C. when protected from light.

The leaflets of Fosfomycin Astro, Fosfomycin Sandoz®, Fosfomycin medicamentum and Fosfomycin Infectopharm® all recommend to use only freshly prepared solution. The chemical stability of the ready-to-use, sterile-prepared fosfomycin solution is indicated to be 24 hours at 25° C. when protected from light.

Quentin et al. (Quentin, Claudine, et al. "Stability of fosfomycin and quinolones in peritoneal dialysis solution." Journal of Antimicrobial Chemotherapy 25.5 (1990): 878-880) comes to the conclusion that certain fosfomycin solutions are stable for 24 hours at room temperature.

Bailie et al. (Bailie, George R., and Michael P. Kane. "Stability of drug additives to peritoneal dialysate." Peritoneal dialysis international 15.8 (1995): 328-335.) also indicate the same results.

The following documents also do not anticipate the present invention, because they do not contain any concrete disclosure with respect to the present invention, nor do they lead up to it, because they provide the skilled person with no concrete clues with respect to the present invention.

WO 2014/040947 A1 refers to a an aerosol supply device having an opening element. In this document, fosfomycin is mentioned as one among hundreds of most varied active substances which can optionally be administered by using the aerosol supply device. For example, the particular combination of the closed container, water, a pharmaceutically acceptable salt of fosfomycin and a pharmaceutically acceptable acid is not disclosed therein.

The same applies to EP 2062608 A2, which discloses a disposable glass vial for a device for generating aerosols.

WO 2008/071197 A1 refers to methods for the treatment of cystic fibrosis or bacterial pneumonia by the pulmonary administration of fosfomycin, but the specific combination of the closed container, water, a pharmaceutically acceptable salt of fosfomycin and a pharmaceutically acceptable acid is not disclosed therein.

WO 2005/110022 A2 relates to a combination of fosfomycin and aminglycoside for the treatment of bacterial respiratory infections. The specific combination of a closed container, water, a pharmaceutically acceptable salt of fosfomycin and a pharmaceutically acceptable acid is not disclosed therein. US 2015/0057242 A1 relates to a combination of fosfomycin and aminoglycoside for the treatment of ventilator associated pneumonia and ventilator associated bronchitis, which is administered by inhalation using a nebulizer and is provided for example in ampoules. However, the document neither discloses the storage conditions for such ampoules (e.g. with regard to storage temperature and duration) nor any test results with regard to the storage stability of fosfomycin.

WO 2012/030513 A2 discloses methods for the treatment of bacterial infections by pulmonary administration of fusidic acid, optionally in combination with tobramycin, amikacin, fosfomycin or levofloxacin. For fosfomycin, only oral administration and pulmonary administration is proposed (see section "Fosfomycin Dosage Forms", paragraphs [0092] and [0093] of said document), in contrast to others of said active ingredients (see section "Amikacin Dosage Forms" directly before, and section "Levofloxacin Dosage Forms", directly thereafter). For example, the particular combination of the closed container, water, a pharmaceutically acceptable salt of fosfomycin and a pharmaceutically acceptable acid is not disclosed therein.

WO 2004/063036 A1 relates to a security container for biologically active substances and processes for their preparation. In said document, fosfomycin is mentioned as one among thousands of most varied active substances which may be provided in the security container if necessary. For example, the particular combination of the closed container, water, a pharmaceutically acceptable salt of fosfomycin and a pharmaceutically acceptable acid is not disclosed therein.

Finally, WO 2010/048059 A1 relates to combinations of fosfomycin and tobramycin for the treatment or prevention of ophthalmic, otological and dermatological infections. However, the particular combination of the closed container, water, a pharmaceutically acceptable salt of fosfomycin and a pharmaceutically acceptable acid in the same solution is not disclosed therein. Remarkably, it is specifically disclosed in relation to the packaging that fosfomycin is separately stored in a blister pack (i.e. dry) for long-term stabilization and is added to the tobramycin solution just prior to use (page 24, 1st paragraph of that document).

In a preferred embodiment of the present invention, the aqueous solution contained in the closed container of the invention is for infusion or injection into the body of a mammal, especially a human being. Preferably, said mammal or human being is a patient who is suffering from a bacterial infection.

In a further preferred embodiment of the present invention, the aqueous solution is provided for an administration selected from intravenous administration, intramuscular administration, intraosseous administration, intravitreal administration, intraperitoneal administration, and intrathecal administration. Of these, particularly preferred is intravenous administration.

In a most preferred embodiment, the aqueous solution is ready to use for parenteral administration. This means in particular that no dilution, mixing (especially with other substances), dissolution, or reconstitution prior to administration of the solution is required anymore. However, if the solution is not contained in a prefilled syringe or an infusion bag, for example, then it has to be transferred into another container suitable for administration, such as a syringe.

Particularly preferably, the aqueous solution is ready to use for intravenous administration or ready to use for administration by inhalation.

Advantageously, the closed container of the present invention is sealed, inter alia, for reasons of tamper safety and also to prevent the accidental reuse of an already opened and thereby potentially contaminated container. The term "sealed" in the context of the present invention means that an opening of the container which has occurred after sealing is detectable and preferably visible even to the naked eye, whereby said detectability and visibility cannot be reversed without at least some effort or without considerable effort. A person of skill in the art is well-acquainted with the means for sealing in the pharmaceutical field; this includes, for example, release liners, tear labels, void sealing, sealing with zipper perforations, and perforations of screw caps ("freshness seal"). Preferably, the sealing of the closed container of the invention or the container according to the invention complies with the norm DIN EN 16679: 2015-03.

For similar reasons as mentioned in the previous paragraph, inter alia, the container is, in a further preferred embodiment of the present invention, closed in a manner, in which an opening of the container is substantially permanent (i.e. to be reversed only with considerable effort). A typical example is breakable ampoules such as made of plastic or glass. A breakable ampoule is known for example from EP 0 243 580 A1 or EP 0 350 772 A1.

In a further preferred embodiment, the closed container of the invention is selected from:
- an ampoule, in particular made of plastic or glass, preferably a breakable ampoule, in particular made of plastic or glass (any container having a closure, which must be broken up, is encompassed within the context of the present invention by the term "breakable ampoule");
- a puncturable vial (also called "vial"; see e.g. WO 2006/072440 A1), preferably sealed with a protective cap;
- an infusion bag or an infusion bottle (e.g. with a Luer-Lock or rubber plug, optionally with graduation), and
- a syringe, especially a syringe ready for injection. The container may be made of a transparent or non-transparent material. Preferably, the container constitutes a light protection for the solution (in particular in the UV/VIS range). The container may be substantially opaque or opaque (in particular in the UV/VIS range). Preferably, the container is a disposable container or for single use.

It is convenient if the container, especially if it is a vial or an intravenous bag, has an intact septum, for example of rubber, or all the septa of the container are intact.

In a further preferred embodiment of the present invention, the pharmaceutically acceptable salt of fosfomycin is selected from fosfomycin disodium salt, fosfomycin monosodium salt, a potassium salt of fosfomycin, a fosfomycin lithium salt, fosfomycin magnesium salt, and fosfomycin calcium salt. Particularly preferred are the sodium salts, in particular fosfomycin disodium salt.

In a further preferred embodiment, the pharmaceutically acceptable acid is a weak acid or an organic acid, preferably a weak organic acid. Weak acids are particularly preferred for their buffering effect. In particular, the preferable organic acid has a pKa value at 25° C. of 2 to 9, preferably 2.5 to 8, more preferably from 3 to 7, even more preferably from 3.5 to 6.5, in particular from 4 to 6, and preferably all pKa values of the acid (if the acid has multiple pKa values) are, independently of each other, within one of these intervalls. Preferably, the pharmaceutically acceptable acid is tolerated by the veins.

In a further particularly preferred embodiment of the present invention, the pharmaceutically acceptable acid is selected from succinic acid, tartaric acid, lactic acid, malic acid, citric acid, carbonic acid, amino acids, acetic acid, and phosphoric acid. Succinic acid is most preferred, especially for intravenous administration.

It is convenient if in the aqueous solution contained in the closed container of the invention essentially the following components are dissolved: a pharmaceutically acceptable salt of fosfomycin and a pharmaceutically acceptable acid, optionally with glucose or fructose (for example in a concentration of 1% to 5% w/v).

In a further preferred embodiment, the aqueous solution contains only fosfomycin as an antibiotic. Preferably the aqueous solution contains just fosfomycin as the only active ingredient (with the pharmaceutically acceptable acid as an adjuvant), optionally with further excipients, in particular glucose or fructose (e.g. in a concentration of 1% to 5% w/v).

In a highly preferred embodiment of the present invention, essentially only fosfomycin disodium salt and succinic acid are dissolved in the aqueous solution, optionally with glucose or fructose (e.g. in a concentration of 1% to 5% w/v).

In a further preferred embodiment, the aqueous solution has a pH (preferably at 25° C.) of less than 10.0, preferably of less than 9.0, more preferably of less than 8.5, even more preferably of less than 8.0, in particular of less than 7.75, or even of at most 7.5.

In a further preferred embodiment the aqueous solution has a pH (preferably at 25° C.) of 3 to 9, preferably from 4 to 8.5, more preferably from 5 to 8.5, in particular from 6 to less than 8.0.

In a further particularly preferred embodiment, the aqueous solution has a pH (preferably at 25° C.) of 6.4 to 8.4, preferably of greater than 6.5 and less than 8.0, more preferably of 6.9 to 7.9, more preferably of 7.0 to 7.8, even more preferred of 7.1 to 7.7, in particular of 7.2 to 7.6 or even of 7.3 to 7.5. In particular this embodiment is suitable for infusion or injection or intravenous administration, with pH values that are as close to the normal pH of human blood (7.35-7.45) as possible being particularly suitable.

In a further preferred embodiment, the aqueous solution (especially when ready to use for intravenous administration) has an osmolarity of at most 800 mosmol/L, preferably at most 600 mosmol/L, more preferably at most 500 mosmol/L, even more preferably at most 450 mosmol/L, especially at most 400 mosmol/L, or even at most 350 mosmol/L; preferably at a certain minimum osmolarity of, for example, at least 50 mosmol/L, at least 100 mosmol/L, or at least 200 mosmol/L. Most preferably, the solution is isotonic or hypotonic (in respect to human blood plasma), preferably at a certain minimum osmolarity of, for example, at least 50 mosmol/L, at least 100 mosmol/L, or at least 200 mosmol/L.

Advantageously, the aqueous solution in the closed container of the present invention contains a total dose of fosfomycin equivalent to 0.25 to 15 grams of fosfomycin, preferably 0.5 to 10 grams of fosfomycin, more preferably from 0.75 to 8 grams of fosfomycin, particularly from 1 to 4 grams of fosfomycin. In particular, the solution is provided as a single dose. Preferably, the volume of the solution (in particular when it is present ready for use) is between 1 ml and 100 ml/g of fosfomycin, preferably between 5 ml and 50 ml/g of fosfomycin, more preferably between 10 ml and 40 ml/g of fosfomycin, even more preferably between 22.5 ml and 27.5 ml/g of fosfomycin, in particular at substantially 25 ml/g of fosfomycin.

In a further preferred embodiment, the pharmaceutically acceptable acid is succinic acid and the mass ratio of succinic acid to fosfomycin in the solution is between 30:1 and 50:1, in particular essentially 40:1.

It is convenient if the closed container of the invention has been sterile filled with the solution. In particular, the closed container is in accordance with the "EU Guidelines for Good Manufacturing Practice for Medicinal Products for Human and Veterinary Use", applicable on 15 Feb. 2016, in particular to Annex 1, in the version of "25 Nov. 2008 (rev.)".

In a further preferred embodiment, the container has been filled with the aqueous solution and closed according to Annex 1 of the "EU Guidelines for Good Manufacturing Practice for Medicinal Products for Human and Veterinary Use", as amended on "25 Nov. 2008 (rev.)".

Due to the surprising finding that fosfomycin is so stable in solution, it is now possible to provide it in the industrial production in solution with an antifungal agent (in particular, ready to use for parenteral or inhalation administration). Such a combination product is particularly suitable for patients with cystic fibrosis (mucoviscidosis), the respiratory tract and lungs of whom are vulnerable to infections by bacteria and fungi. It is therefore preferred if the solution in the closed container further comprises an antifungal agent which is preferably selected from the group consisting of terbinafine, naftifine, butenafine, and pharmaceutically acceptable salts thereof. The solution may have a total dose of 10 mg to 5000 mg, preferably from 20 mg to 2000 mg, more preferably from 30 mg to 1000 mg, even more preferably from 40 mg to 500 mg, in particular from 50 mg to 250 mg of said antifungal agent.

In a particularly preferred embodiment, the antifungal agent is terbinafine or a pharmaceutically acceptable salt thereof. It is preferred that the solution contains a total dose of terbinafine equivalent to 10 mg to 2000 mg of terbinafine, preferably from 20 mg to 1000 mg of terbinafine, more preferably from 30 mg to 500 mg of terbinafine, even more preferably from 40 mg to 250 mg of terbinafine, in particular from 50 mg to 200 mg, or even from 50 mg to 100 mg of terbinafine. The mass ratio of terbinafine to fosfomycin in the solution is usually between 1:1 and 1:200, preferably between 1:2 and 1:100, more preferably between 1:3 and 1:75, even more preferably between 1:4 and 1:50, in particular between 1:5 to 1:25.

In a further aspect, the present invention relates to a package comprising at least one closed container of the invention. The package may be made, inter alia, from cardboard, especially from printed cardboard. The package preferably comprises a leaflet. Preferably, the package constitutes a light protection for the solution or the container (especially in the UV/VIS range). The package may be substantially opaque or opaque (in particular in the UV/VIS range). Preferably, the package additionally preserves the sterility of the closed container (and thus its outer surface), for example when the package or a part thereof is constructed as a plastic film.

Advantageously, the package of the invention is sealed, among other things for reasons of security against manipulation or also to prevent accidental reuse. The term "sealed" means in this context that an opening of the package, which took place after the sealing, is detectable, and preferably visible even to the naked eye, wherein said detectability and visibility cannot be reversed at least not without effort or without substantial effort. To the skilled person, the means for sealing of packages in the pharmaceutical field are known, and these include, for example, release liners, tear labels and VOID seals. Preferably, the sealing of the package of the invention or the packaging of the invention complies with the standard of DIN EN 16679:2015-03.

In a particularly preferred embodiment, the package further comprises an antifungal agent, in particular terbinafine. Typically, the antifungal agent is contained in the solution of fosfomycin.

In a further aspect, the present invention relates to the storing of the closed container of the invention or the package of the invention at a temperature of between 0° C. and 60° C., in particular at a temperature of 15° C. to 35° C. or at room temperature, for at least one week, preferably for at least one month, more preferably for at least three months, even more preferably for at least six months, especially for at least one year or even for at least two years. Preferably, the storing takes place under light protection (in particular in the UV/VIS range).

In a further aspect, the present invention relates to a process comprising sterile filling the container with the solution and closing the container. Preferred for a further step is sealing the closed container, in particular according to the standard of DIN EN 16679:2015-03.

Preferably, the aqueous solution is not produced from a sterile mixed powder mixture of the pharmaceutically acceptable salt of fosfomycin and a pharmaceutically acceptable acid in accordance with the "EU Guidelines for Good Manufacturing Practice for Medicinal Products for Human and Veterinary Use", applicable on 15 Feb. 2016, especially in accordance with Annex 1 in the version of "25 Nov. 2008 (rev.)".

In a further aspect, the present invention relates to a process for the production of the package of the invention, comprising carrying out the method of the invention for the preparation of the closed container of the invention and the packing of the closed container into the package. Preferred for a further step is the sealing of the package, in particular according to the standard of DIN EN 16679:2015-03.

In a further aspect, the present invention relates to fosfomycin for use in the prevention or treatment of an infection, particularly an infection of the lower respiratory tract or the lung, in a patient suffering from cystic fibrosis. Such patients are particularly susceptible to respiratory or lung infections by bacteria or fungi which may occur repeatedly and may frequently become chronic. An overview of these issues is provided, for example, by Lyczak et al. ("Lung infections associated with cystic fibrosis." Clinical Microbiology Reviews 15.2 (2002): 194-222.) or Gibson et al. ("Pathophysiology and management of pulmonary infections in cystic fibrosis." American Journal of Respiratory and Critical Care Medicine 168.8 (2003): 918-951. Because of the increased risk in terms of resistance, it is especially useful to also have available comparatively rather uncommon antibiotics such as fosfomycin (or in systemic use comparatively rather uncommon antifungal agents such as terbinafine), which are already in solution for easy use (or even ready to use for parenteral or inhalation administration), as is achieved by the present invention. In addition, the use of lower doses or a more targeted application is enabled thereby, which in turn reduces the risk of resistances.

In this aspect, fosfomycin or a pharmaceutically acceptable salt thereof is usually administered in a solution parenterally, intravenously or by inhalation to the patient. Optionally, the solution also comprises an antifungal agent.

In a particularly preferred embodiment, fosfomycin or a pharmaceutically acceptable salt thereof is administered together with terbinafine or a pharmaceutically acceptable salt thereof to the patient. Typically, at least one of the administrations is parenterally or by inhalation. It is convenient if fosfomycin or a pharmaceutically acceptable salt thereof, and terbinafine, or a pharmaceutically acceptable salt thereof is provided in the same aqueous solution for a (preferably parenteral, in particular inhalative) administration.

Further definitions:

Herein, "parenteral" must be interpreted in its broadest sense (bypassing of the intestine), i.e. all modes of administration other than the oral or rectal are encompassed by this term.

The aqueous solution is preferably liquid within the meaning of the present invention. In particular, it is not substantially different from water with respect to its viscosity at the same temperature. Preferably, the viscosity of the solution at 20° C. and normal pressure is between 0.5 cP and 25 cP, preferably at about 1-2 cP, in particular at about 1 cP. Preferably, the aqueous solution is not a suspension, emulsion, cream or gel.

Preferably, the water in the aqueous solution is water for injection, in particular in accordance with Ph. Eur. (8th edition).

The present invention particularly relates to the following preferred embodiments:

Embodiment 1. A closed container, comprising an aqueous solution for parenteral administration, wherein at least a pharmaceutically acceptable salt of fosfomycin and a pharmaceutically acceptable acid are dissolved in the solution.

Embodiment 2. A closed container according to embodiment 1, wherein said solution is ready to use for parenteral administration.

Embodiment 3. A closed container according to embodiment 2, wherein the solution is ready to use for intravenous administration or ready to use for parenteral administration.

Embodiment 4. A closed container according to any one of embodiments 1 to 3, wherein the closed container is sealed.

Embodiment 5. A closed container according to any one of embodiments 1 to 4, wherein the container is closed in a manner that an opening of the container is substantially irreversible.

Embodiment 6. A closed container according to any one of embodiments 1 to 5, wherein the container is selected from:
an ampoule in particular made of plastic or glass, preferably a breakable ampoule in particular made of plastic or glass,
a puncturable vial, preferably sealed with a cap,
an infusion bag, and
a syringe, especially a syringe ready for injection.

Embodiment 7. A closed container according to any one of embodiments 1 to 6, wherein the container, which preferably is a puncturable vial or an infusion bag, has an intact septum for example made of rubber.

Embodiment 8. A closed container according to any one of embodiments 1 to 7, wherein the container serves as a light protection for the solution, and in particular is substantially opaque.

Embodiment 9. A closed container according to any one of embodiments 1 to 8, wherein the pharmaceutically acceptable salt of fosfomycin is selected from fosfomycin disodium salt, fosfomycin monosodium salt, a fosfomycin potassium salt, a fosfomycin lithium salt, fosfomycin magnesium salt, and fosfomycin calcium salt.

Embodiment 10. A closed container according to any one of embodiments 1 to 9, wherein the pharmaceutically acceptable acid has a pKa value at 25° C. of 2 to 9, wherein the acid is preferably selected from succinic acid, tartaric acid, lactic acid, malic acid, citric acid, carbonic acid, amino acids, acetic acid, and phosphoric acid.

Embodiment 11. A closed container according to any one of embodiments 1 to 10, wherein the only dissolved components in the solution are, in essence, a pharmaceutically acceptable salt of fosfomycin and a pharmaceutically acceptable acid, optionally with glucose or fructose.

Embodiment 12. A closed container according to embodiment 11, wherein only fosfomycin disodium salt and succinic acid are dissolved in the solution, in essence, optionally with glucose or fructose.

Embodiment 13. A closed container according to any one of embodiments 1 to 12, wherein the solution (preferably at 25° C.) has a pH value of 6.4 to 8.4, preferably of greater than 6.5 and less than 8.0, more preferably from 6.9 to 7.9, more preferably from 7.0 to 7.8, even more preferably from 7.1 to 7.7, in particular from 7.2 to 7.6 or even from 7.3 to 7.5; or wherein the solution (preferably at 25° C.) has a pH of less than 10.0, preferably of less than 9.0, more preferably of less than 8.5, even more preferably of less than 8.0, in particular of less than 7.75 oder even of at most 7.5; or wherein the solution (preferably at 25° C.) has a pH of 3 to 9, preferably of 4 to 8.5, more preferably from 5 to 8.5, in particular from 6 to less than 8.0.

Embodiment 14. A closed container according to any one of embodiments 1 to 13, wherein the solution contains a total dose of fosfomycin equivalent to 0.25 to 15 grams of fosfomycin, preferably from 0.5 to 10 grams of fosfomycin, more preferably from 0.75 to 8 grams of fosfomycin, in particular from 1 to 4 grams of fosfomycin.

Embodiment 15. A closed container according to any one of embodiments 1 to 14, wherein said pharmaceutically acceptable acid is succinic acid and the mass ratio of succinic acid to fosfomycin in the solution is between 30:1 and 50:1, in particular at substantially 40:1.

Embodiment 16. A closed container according to any one of embodiments 1 to 15, wherein the container has been sterile filled with the solution.

Embodiment 17. A closed container according to any one of embodiments 1 to 16, wherein the closed container in accordance with the "EU Guidelines for Good Manufacturing Practice for Medicinal Products for Human and Veterinary Use", applicable on 15 Feb. 2016, in particular to Annex 1 in the version of "25 Nov. 2008 (rev.)".

Embodiment 18. A closed container according to any one of embodiments 1 to 17, wherein the container has been filled with the solution and closed according to Annex 1 of the "EU Guidelines for Good Manufacturing Practice for Medicinal Products for Human and Veterinary Use" in the version of "25 Nov. 2008 (rev.)".

Embodiment 19. A closed container according to any one of embodiments 1 to 10 and 13 to 18, wherein the solution further comprises an antifungal agent dissolved in it.

Embodiment 20. A closed container according to embodiment 19, wherein the antifungal agent is selected from the group consisting of terbinafine, naftifine, butenafine, and pharmaceutically acceptable salts thereof.

Embodiment 21. A closed container according to embodiment 20, wherein the antifungal agent is terbinafine or a pharmaceutically acceptable salt thereof.

Embodiment 22. A closed container according to any one of embodiments 19 to 21, wherein the solution contains a total dose of 10 mg to 5000 mg, preferably of 20 mg to 2000 mg, more preferably of 30 mg to 1000 mg, even more preferably of 40 mg to 500 mg, in particular of 50 mg to 250 mg of the antifungal agent.

Embodiment 23. A closed container according to embodiment 21, wherein the solution contains a total dose of terbinafine equivalent to 10 mg to 2000 mg of terbinafine, preferably to 20 mg to 1000 mg of terbinafine, more preferably to 30 mg to 500 mg of terbinafine, even more preferably of 40 mg to 250 mg of terbinafine, in particular of 50 mg to 200 mg or even of 50 mg to 100 mg of terbinafine.

Embodiment 24. A closed container according to embodiment 21, wherein the mass ratio of terbinafine to fosfomycin in the solution is between 1:1 and 1:200, preferably between 1:2 and 1:100, more preferably between 1:3 and 1:75, even more preferably between 1:4 and 1:50, in particular between 1:5 and 1:25.

Embodiment 25. A package comprising at least one closed container according to any one of embodiments 1 to 18 and preferably a leaflet.

Embodiment 26. A package according to embodiment 25, further comprising an antifungal agent, in particular terbinafine, preferably wherein the antifungal agent is present as defined in one of the embodiments 19 to 24.

Embodiment 27. A package according to embodiment 25 or 26, wherein the package serves as a light protection for the solution or the closed container, and is in particular substantially opaque.

Embodiment 28. A method comprising the storing of the closed container of one of the embodiments 1 bis 24 or the package of one of the embodiments 25 to 27 at a temperature between 0° C. and 60° C., in particular at a temperature of 15° C. to 35° C. or at room temperature, for at least one week, preferably for at least one month, more preferably for at least three months, even more preferably for at least six months, in particular for at least one year, or even for at least two years.

Embodiment 29. A method for the production of the closed container of any one of embodiments 1 to 24, comprising sterile filling the container with the solution and closing the container.

Embodiment 30. The method of producing according to embodiment 29, further comprising sealing the closed container.

Embodiment 31. The method of production according to any one of embodiments 29 to 30, wherein the solution is not produced of a sterile mixed powder mixture in accordance with "EU Guidelines for Good Manufacturing Practice for Medicinal Products for Human and Veterinary Use", applicable on 15 Feb. 2016, and in particular in accordance with Annex 1 in the version of "25 Nov. 2008 (rev.)", of the pharmaceutically acceptable fosfomycin salt and the pharmaceutically acceptable acid Embodiment 32. A method for the production of the package according to any one of embodiments 25 to 27, comprising performing the method according to any one of embodiments 29 to 31, whereby said closed container is obtained, and packing the closed container into the package.

Embodiment 33. Fosfomycin for use in the prevention or treatment of an infection, particularly an infection of the lower respiratory tract, in a patient suffering from cystic fibrosis, wherein the fosfomycin or a pharmaceutically acceptable salt thereof is administered parenterally, in particular intravenously or by inhalation, in a solution, as defined in any one of embodiments 1 to 18.

Embodiment 34. Fosfomycin for use in the prevention or treatment of an infection, particularly an infection of the lower respiratory tract, in a patient suffering from cystic fibrosis, wherein the fosfomycin or a pharmaceutically acceptable salt thereof together with an antifungal agent is administered parenterally, in particular intravenously or by inhalation, in a solution, as defined in any one of embodiments 19 to 24.

Embodiment 35. Fosfomycin for use in the prevention or treatment of an infection, particularly an infection of the lower respiratory tract, in a patient suffering from cystic fibrosis, wherein the fosfomycin or a pharmaceutically acceptable salt thereof together with terbinafine or a pharmaceutically acceptable salt thereof is administered parenterally, in particular intravenously or by inhalation, to the patient.

Embodiment 36. Fosfomycin for use according to embodiment 35, wherein fosfomycin or a pharmaceutically acceptable salt thereof and terbinafine or a pharmaceutically acceptable salt thereof is present in the same aqueous solution for administration.

BRIEF DESCRIPTION OF THE DRAWINGS

The invention is further illustrated by the following examples and figures to which it is of course not limited.

DETAILED DESCRIPTION OF THE INVENTION

Example 1—Preparation

Figure 1A:
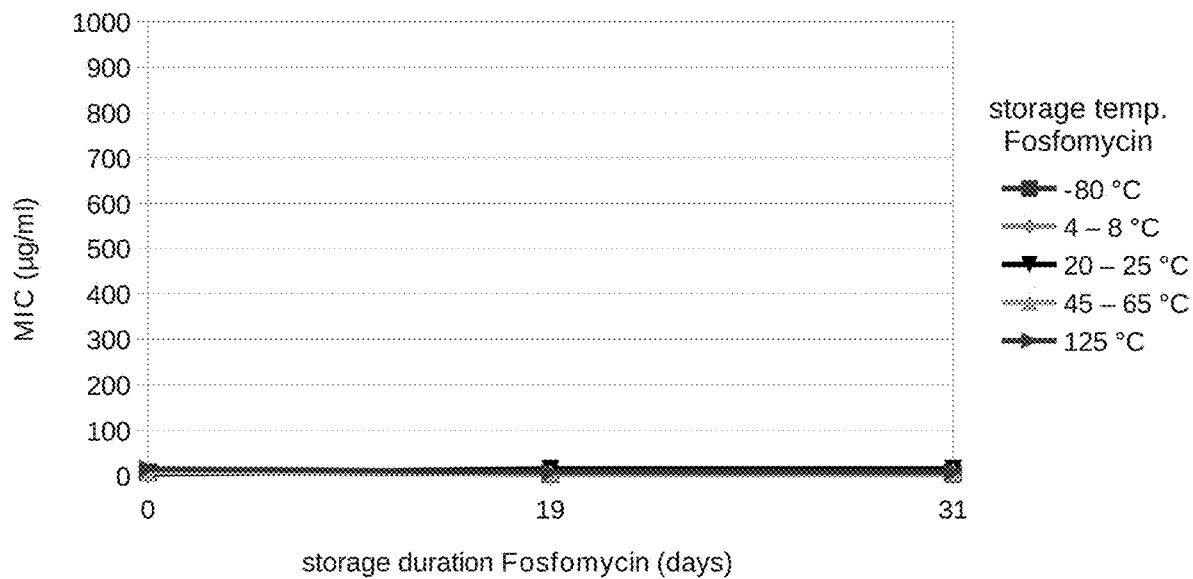
FIGS. 1A-1D: Minimal Inhibitory Concentration (MIC) of a fosfomycin acid solution as a function of storage time and temperature with respect to *Staphylococcus aureus* ATTC 49775 (FIG. 1A), *Staphylococcus aureus* ATTC 33592 (FIG. 1B), *Staphylococcus hominis* AG 1115 (FIG. 1C) and *Escherichia coli* AG 1215 (FIG. 1D). The lower the MIC of an antibiotic, the stronger the antimicrobial effect of the antibiotic, as is well known. The MIC values measured in the course of the present invention against the tested bacterial strains compared to the initial value were in the normal range of distribution of the experimental set-up, i.e. surprisingly, no degradation of the MIC due to storage could be observed within the observational period. Thus, a solution of fosfomycin and an acid at room temperature (and even with autoclaving or with extreme temperature conditions) will maintain its antimicrobial activity over a period of at least three months, which contradicts a strongly anchored prejudice in the art stating that fosfomycin is unstable.

In 500 L of water for injection in accordance with Ph. Eur. (8th edition), 26.4 kg of fosfomycin disodium (corresponding to 20 kg of fosfomycin) and 500 g of succinic acid are dissolved under sterile conditions. This solution is filled under sterile conditions in 5000 infusions bottles (single volume 100 ml). The infusion bottles are each capped with a suitable rubber stopper and packaged at 10 pieces per box.

The pH of this solution is 7.5. The solution contained in the infusion bags is ready to use for intravenous administration and is storable at room temperature for months. When fosfomycin produced by fermentation is used, a sterile filter is inserted upstream in the final fill into the infusion bottle under sterile conditions.

Example 2—Stability Studies

The objective of the present investigation was to find out whether the antimicrobial activity of fosfomycin with a pH suitable for intravenous administration is maintained in a solvent suitable for intravenous use. For this, fosfomycin disodium (14.5 mmol sodium/g) and succinic acid were used to adjust the pH (0.025 grams of succinic acid per gram of fosfomycin).

The pH of this solution was 7.5.

A stock solution of 4 g of fosfomycin disodium and succinic acid (0.025 grams of succinic acid per gram of fosfomycin, corresponding to about 3 g of fosfomycin) in 10 ml distilled water was prepared and divided into 5 cryotubes at 2 ml each, and the solution was exposed at different temperatures as follows:

Aliquots of 2 ml of the sample were stored at −80° C., at refrigerator temperature (2-8° C.), at room temperature (20-25° C.), and at 45-65° C. until the test end. Another 2 ml of the stock solution were stored at refrigerator temperature (2-8° C.) and autoclaved before the tests at 125° C. for 30 minutes. After that, all samples were tested for their antimicrobial activity.

To determine the antimicrobial activity of fosfomycin, the minimal inhibitory concentration (MIC) of the 4 mentioned bacteria strains was determined by a tube dilution method in microtiter plates using Mueller-Hinton broth. For the inoculation of the microtiter plates, the inoculum was adjusted to 1.5×104 germs/ml. The evaluation was made after 24 hours of incubation at 37° C.

Samples were taken, starting with 2,000 µg/ml test substance, diluted by a factor 2. Serial dilutions of 2,000 µg/ml to 1.95 µg/l were prepared. For the detection of the antimicrobial activity and the stability of a solution of fosfomycin and succinic acid in a solvent suitable for intravenous administration, the MIC values were determined after incubation for 24 hours at 37° C.

The following bacterial strains were used in the studies:
Staphylococcus aureus No. ATCC 49775,
Staphylococcus aureus No. ATCC 33592,
Staphylococcus hominis No. ATCC 1115, and
Escherichia coli No. AG 1215.

Figure 1B:
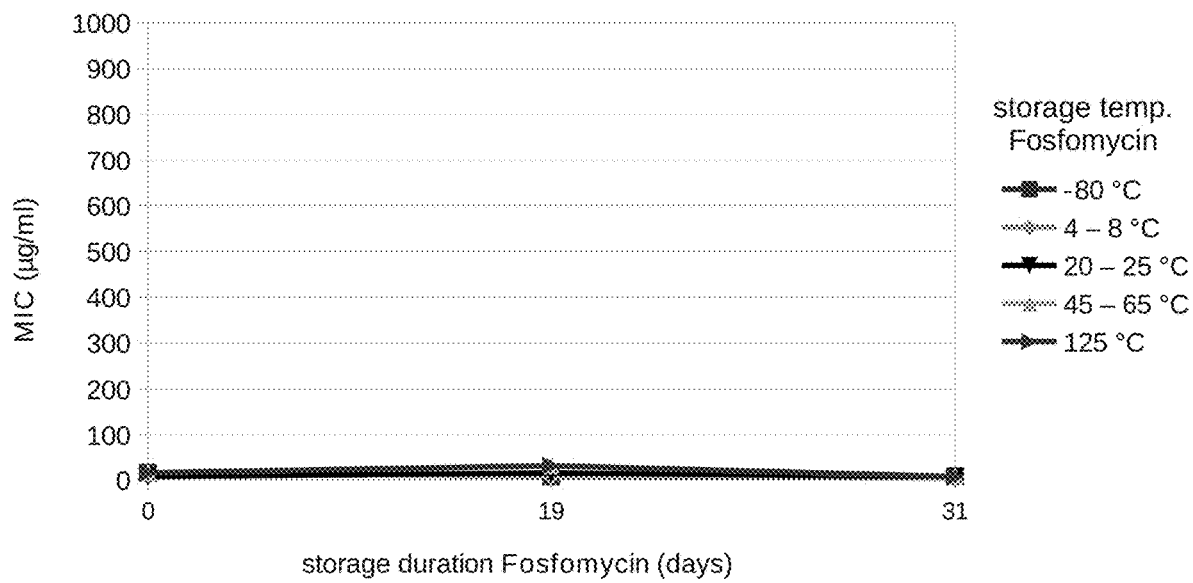
Figure 1C:
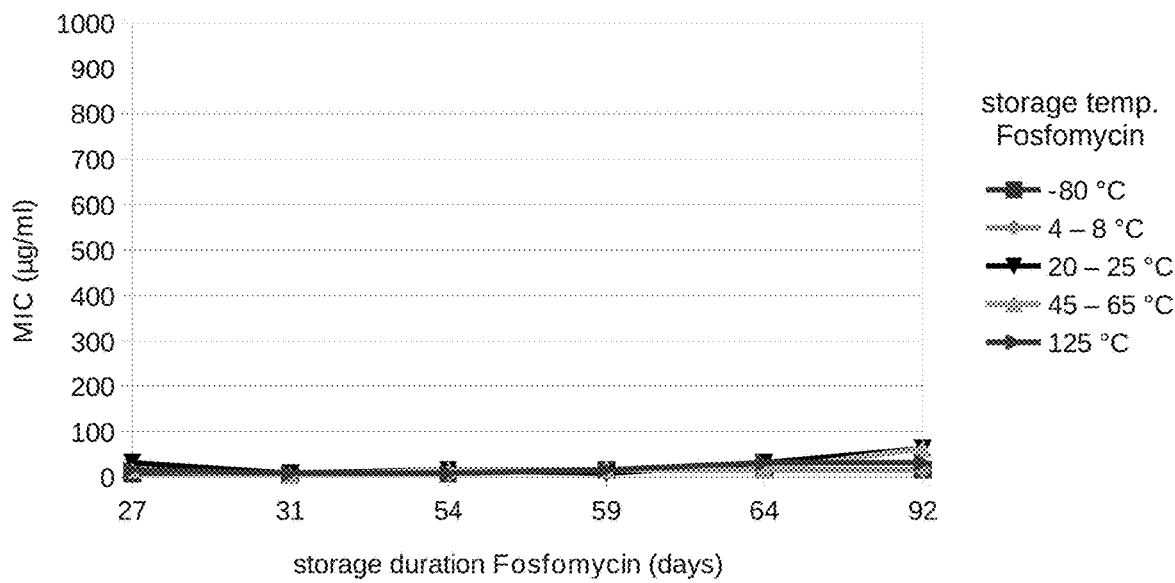
Figure 1D:
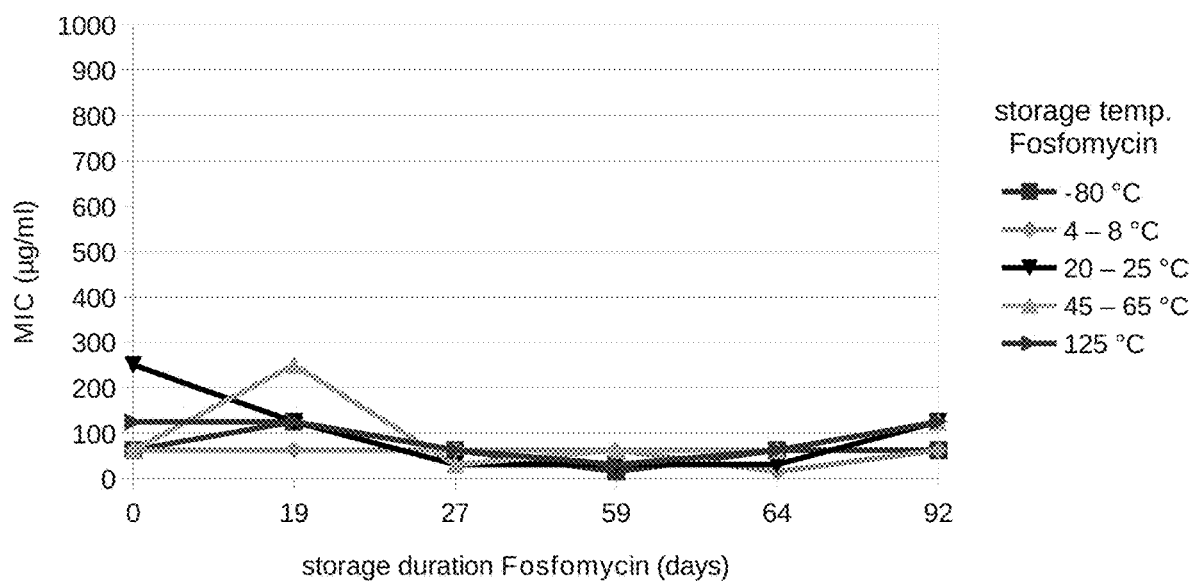

The results are shown in Table 1 and are illustrated in FIGS. 1A-1D. The measured values of MIC against the tested bacteria compared to the initial value are within the normal range of distribution of the experimental set-up, i.e. surprisingly, no degradation of the MIC due to storage could be observed within the observational period. Thus, a solution of fosfomycin and an acid at room temperature will maintain (and even with autoclaving or with extreme temperature conditions) its antimicrobial activity over a period of at least three months, which contradicts a strongly anchored prejudice in the art stating that fosfomycin is unstable.

TABLE 1

The table shows the MIC values of the tested bacterial strains dependent on the storage conditions of fosfomycin (duration and temperature). Storage-dependent minimal inhibitory concentrations (µg/ml) of Fosfomycin

| Storage temp. (° C.) | Storage period of Fosfomycin in days | | | | | | | |
|---|---|---|---|---|---|---|---|---|
| | 0 | 19 | 27 | 31 | 54 | 59 | 64 | 92 |
| Staphylococcus aureus ATTG 49775 | | | | | | | | |
| −80 | 7.8 | 3.9 | — | 3.9 | — | — | — | — |
| 4-8 | 7.8 | 3.9 | — | 3.9 | — | — | — | — |
| 20-25 | 3.9 | 15.6 | — | 15.6 | — | — | — | — |
| 45-65 | 7.8 | 7.8 | — | 7.8 | — | — | — | — |
| 125 | 15.6 | 7.8 | — | 7.8 | — | — | — | — |
| Staphylococcus aureus ATTC 33592 | | | | | | | | |
| −80 | 15.6 | 7.8 | — | 7.8 | — | — | — | — |
| 4-8 | 15.6 | 7.8 | — | 3.9 | — | — | — | — |
| 20-25 | 7.8 | 15.6 | — | 7.8 | — | — | — | — |
| 45-65 | 15.6 | 31.2 | — | 7.8 | — | — | — | — |
| 125 | 15.6 | 31.2 | — | 7.8 | — | — | — | — |
| Staphylococcus hominis AG 1115 | | | | | | | | |
| −80 | — | — | 7.8 | 7.8 | 7.8 | 15.6 | 15.6 | 15.6 |
| 4-8 | — | — | 15.6 | 7.8 | 7.8 | 15.6 | 15.6 | 15.6 |
| 20-25 | — | — | 31.2 | 7.8 | 15.6 | 7.8 | 31.2 | 62.5 |
| 45-65 | — | — | 15.6 | 3.9 | 15.6 | 15.6 | 15.6 | 62.5 |
| 125 | — | — | 15.6 | 7.8 | 7.8 | 15.6 | 31.2 | 31.2 |
| Escherichia coli AG 1215 | | | | | | | | |
| −80 | 62.5 | 125.0 | 62.5 | — | — | 15.6 | 62.5 | 62.5 |
| 4-8 | 62.5 | 62.5 | 62.5 | — | — | 62.5 | 15.6 | 62.5 |
| 20-25 | 250.0 | 125.0 | 31.2 | — | — | 31.2 | 31.2 | 125.0 |
| 45-65 | 62.5 | 250.0 | 31.2 | — | — | 62.5 | 62.5 | 125.0 |
| 125 | 125.0 | 125.0 | 62.5 | — | — | 31.2 | 62.5 | 125.0 |

Example 3—Preparation of the Combination Preparation of Fosfomycin and Terbinafine 26.4 kg of fosfomycin disodium (corresponding to 20 kg of fosfomycin), 500 g of succinic acid and 0.5 kg of terbinafine HCl are dissolved under sterile conditions in 500 L of water for injection in accordance with Ph. Eur. (8th Edition). This solution is bottled under sterile conditions in 50,000 bottles (single volume: 10 ml). The bottles are each sealed with appropriate rubber stoppers and are packaged into a box at 50 pieces each.

The solution contained in the bottles is ready to use for administration by inhalation as an aerosol and can be stored at room temperature for months.

The invention claimed is:

1. A closed container, comprising an aqueous solution for parenteral administration, wherein at least a pharmaceutically acceptable salt of fosfomycin and a pharmaceutically acceptable acid are dissolved in the solution, wherein the acid is selected from succinic acid, tartaric acid, lactic acid, malic acid, citric acid, carbonic acid, amino acids, acetic acid, and phosphoric acid.

2. The closed container according to claim 1, wherein the solution is ready to use for parenteral administration.

3. The closed container according to claim 2, wherein the solution is ready to use for intravenous administration.

4. The closed container according to claim 1, wherein the closed container is sealed, wherein the container is closed in a manner such that opening of the container is substantially irreversible.

5. The closed container according to claim 1, wherein the container is selected from:
   an ampoule, or a breakable ampule,
   a puncturable vial, optionally sealed with a protective cap,
   an infusion bag, and
   a syringe, optionally a syringe ready for injection.

6. The closed container according to claim 1, wherein the container is a puncturable vial or an infusion bag and has an intact septum.

7. The closed container according to claim 1, wherein the container serves as a light protection for the solution.

8. The closed container according to claim 1, wherein the pharmaceutically acceptable salt of fosfomycin is selected from fosfomycin disodium salt, fosfomycin monosodium salt, a fosfomycin potassium salt, a fosfomycin lithium salt, fosfomycin magnesium salt, and fosfomycin calcium salt.

9. The closed container according to claim 1, wherein the solution has a pH value of 6.4 to 8.4.

10. The closed container according to claim 1, wherein the pharmaceutically acceptable acid is succinic acid and the mass ratio of succinic acid to fosfomycin in the solution is between 30:1 and 50:1.

11. The closed container according to claim 1, and a leaflet, wherein the closed container is enclosed in a package that protects the solution or the closed container from light.

12. A method for producing the closed container according to claim 1, the method comprising filling the container with the solution in a sterile manner and closing the container.

13. A closed infusion container, comprising an aqueous solution ready to use for intravenous administration, wherein at least a pharmaceutically acceptable salt of fosfomycin and a pharmaceutically acceptable acid are dissolved in the solution, wherein the solution contains a total dose of fosfomycin equivalent to 1 to 15 grams of Fosfomycin, wherein the acid is selected from succinic acid, tartaric acid, lactic acid, malic acid, citric acid, carbonic acid, amino acids, acetic acid, and phosphoric acid.

14. The closed infusion container of claim 13, wherein the container is a bag, and the bag is in a package with a leaflet, wherein the package is substantially opaque.

15. The method of claim 12, further comprising sealing the closed container.

* * * * *